United States Patent
Konya et al.

(10) Patent No.: US 6,258,114 B1
(45) Date of Patent: *Jul. 10, 2001

(54) HOOP STENT

(75) Inventors: Andras Konya; Sidney Wallace; Kenneth C. Wright, all of Houston, TX (US)

(73) Assignee: Micro Therapeutics, Inc., Irvine, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/185,868

(22) Filed: Nov. 3, 1998

Related U.S. Application Data

(63) Continuation of application No. 08/813,614, filed on Mar. 7, 1997, now Pat. No. 5,830,229.

(51) Int. Cl.[7] .................................................. A61M 29/00
(52) U.S. Cl. ............................................ 606/198; 606/194
(58) Field of Search ..................................... 606/194, 198, 606/191; 623/1, 12

(56) References Cited

U.S. PATENT DOCUMENTS

| | | | |
|---|---|---|---|
| 4,512,338 | 4/1985 | Balko | 128/1 R |
| 4,800,882 | 1/1989 | Gianturco | 128/343 |
| 4,856,516 | * 8/1989 | Hillstead | 623/1 |
| 4,913,141 | * 4/1990 | Hillstead | 606/108 |
| 5,135,536 | 8/1992 | Hillstead | 606/195 |
| 5,554,181 | * 9/1996 | Das | 606/194 |
| 5,575,816 | 11/1996 | Rudnik | 623/1 |
| 5,578,149 | 11/1996 | De Scheerder | 148/563 |
| 5,766,238 | * 6/1998 | Lau et al. | 606/198 |

OTHER PUBLICATIONS

Cragg, et al., Nonsurgical Placement of Arterial Endoprosthesis: A new Technique Using Nitinol Wire, 147 radiology 261 (Apr. 1983).

Dotter, Transluminal Expandable Nitinal Coil Stent Grafting, 147 radiology 259 (Apr. 1983).

* cited by examiner

*Primary Examiner*—Kevin Truong
(74) *Attorney, Agent, or Firm*—K. David Crockett, Esq.; Crockett & Crockett

(57) ABSTRACT

A wire frame stent and stent delivery system for inserting the stent into the body.

6 Claims, 2 Drawing Sheets

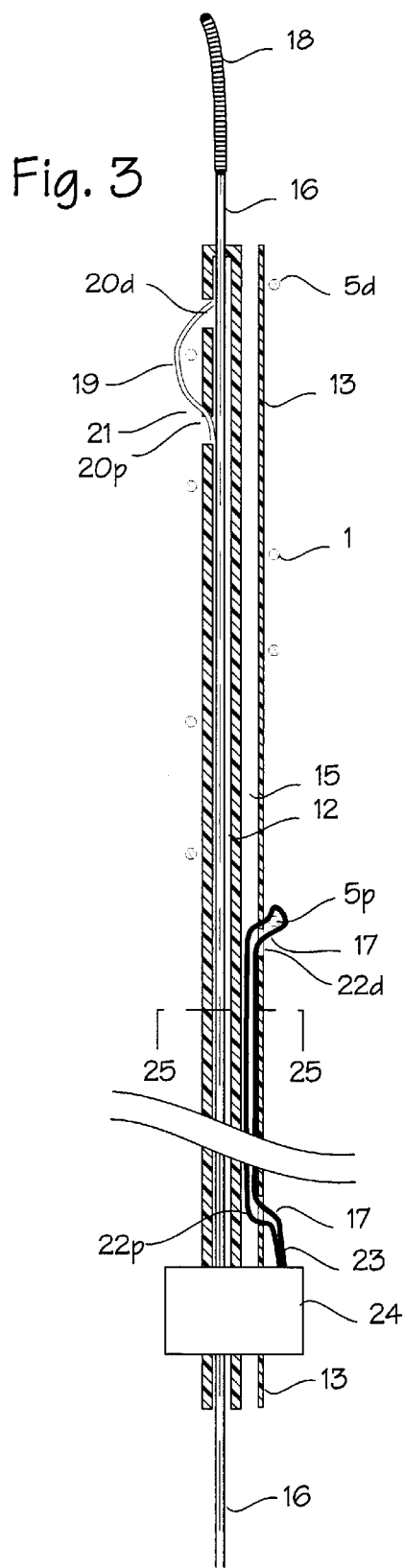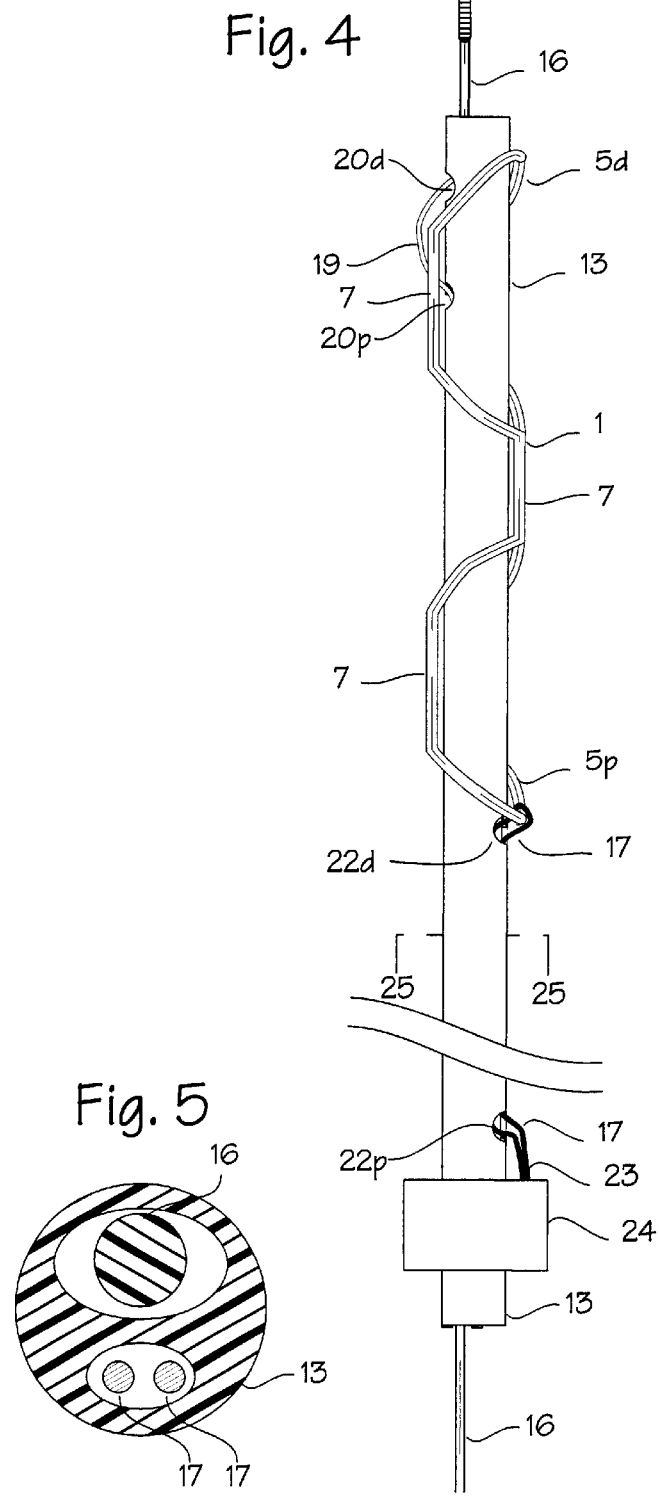
Fig. 3
Fig. 4
Fig. 5

HOOP STENT

This application is a continuation of U.S. application Ser. No. 08/813,614 filed Mar. 7, 1997, now U.S. Pat. No. 5,830,229.

FIELD OF THE INVENTION

This invention relates to stents for use in vascular surgery.

BACKGROUND OF THE INVENTION

A wide variety of stent designs have been proposed for use in the vascular system. Typically, the stents are used to hold open a length of blood vessel which has been closed or occluded by some growth within the blood vessel. Balloon expandable stents and self-expanding stents are commercially available and have been used successfully for treatment of a number vascular diseases. Das, Stent, U.S. Pat. No. 5,554,181 (Sep. 10, 1996) shows a wire stent having a number of hoops all attached to a radially disposed spine, all of which may be formed of a single wire. Likewise, Hillstead, Endovascular Stent Apparatus and Method, U.S. Pat. No. 4,856,516 (Aug. 15, 1989). The stents are folded upon a catheter pusher and retained within a catheter sheath before release into the body. These stents must be radially compressed to fit within the catheter sheath, and expand elastically or may be expanded in elastically by a balloon. They are not susceptible to being stretched or elongated in the along their long axes to reduce their overall diameter.

SUMMARY

The stent and stent delivery system described herein are designed for insertion into blood vessels and other lumens of the body. The self-expandable stent is composed of a single small diameter (0.005 inch) nitinol wire which is doubled first by making a bend at its mid-portion. The wire pair is then led around a tubular jig to form a hoop, and the wires are joined by double twisting or point welding to form a strut, then led around the tubular jig to form another hoop, joined to form another strut, and so on until the desired number of hoops are formed. The stent may be stretched along the long axis of the stent, whereupon the hoops are deformed into ellipses disposed at an angle approximately midway between the long axis of the stent and the radius of the stent, and the overall diameter of the stent is reduced by this deformation.

To deploy the stent, it is stretched out completely on the surface of a small catheter (3-F). The catheter contains a specially designed angled tip guide wire provided with a low-profile hook. The front end of the constrained stent is hung on the hook. The hook comes out from the catheter's lumen through a hole and goes back into the catheter through another hole. A monofilament retrieving loop runs from the proximal end of the deployment catheter to the to the proximal end of the stent. The proximal end of the retrieving loop is fastened to a sliding ring attached to the proximal end of the 3-F catheter shaft. Before final release of the stent, the retrieving loop may be operated via the sliding ring to pull the stent in order to correct for any error in the initial placement of the stent. After the stent is properly placed and the retrieving loop may be severed to release the stent from the delivery catheter. The stent has thermal shape memory or pseudoelasticity which facilitates deployment.

BRIEF DESCRIPTION OF THE DRAWINGS

FIG. 3 is a cross-section of the delivery catheter for use with the stent.

FIG. 4 is a view of the delivery catheter for use with the stent.

FIG. 5 is a radial cross-section of the delivery catheter for use with the stent.

DETAILED DESCRIPTION OF THE INVENTION

Figure 1:
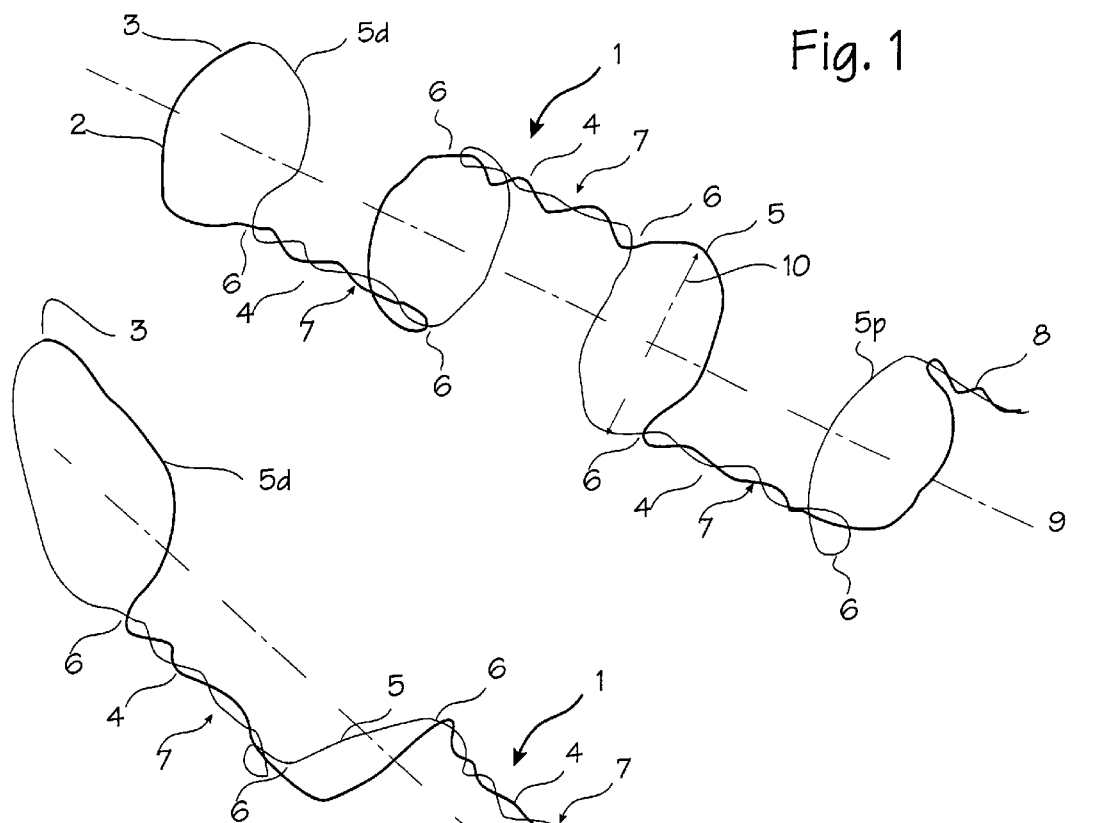
FIG. 1 is a view of the stent.

FIG. 1 shows the stent in its expanded state. The stent 1 is comprised of a single wire 2 which is folded at a point along the wire, such as mid-point 3 to form a length of double wire comprising two wire segments. Several twisted sections 4 in the double wire are interspersed with several hoops 5 formed by pulling the double wire apart into the hoop shape. The double wire is then bent at each junction 6 between the twisted sections and the hoops to form an angle of about 90° between each hoop and twisted section. The twisted sections 4 create alternately radially opposed struts or spines 7 between successive hoops. The free ends 8 of the wire 2 may be twisted into a free spine as shown, or they may be joined together. The hoops in this arrangement are aligned along a common axis 9 which defines the longitudinal axis of the stent, and they are oriented approximately parallel to each other. The stent has an unconstrained diameter defined by hoop diameter 10. The hoops may be all the same overall diameter, or they may be of different diameter, and it may be particularly useful to create the hoops so that the size of the hoops increases from one end of the stent to the other. The struts may be all the same length or of varying length. Although shown as being formed by intertwining the tow wire segments, the struts maybe formed by welding the segments together, or by shaping the segments to run parallel where the strength of the wire permits. Note that the stent may be formed of two separate lengths of wire, but in this case a free end strut at distal hoop 5d, or a joint provided elsewhere along the stent, may be required.

Figure 2:
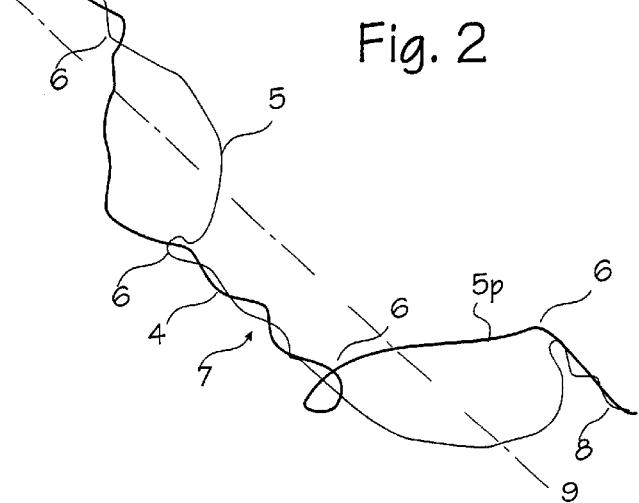
FIG. 2 is a view of the stent in a stretched condition for loading onto the delivery catheter.

FIG. 2 shows the stent stretched out in the condition that it will be loaded onto the delivery catheter. In its stretched condition, the hoops 5 have elongated into reclining ellipses 11 oriented at an angle from the longitudinal axis 9 of the stent 1. The angle is intermediate between the longitudinal axis of the stent and the radius 12 of the stent. Thus the overall diameter of the stent has been significantly reduced by stretching along the longitudinal axis. The fact that the struts are not radially aligned permits longitudinal stretching or deformation of every hoop in the stent. As illustrated, the each strut is radially opposed to the struts on either side, meaning the each strut is on the opposite side of the stent compared to the preceding or succeeding strut. When the adjacent struts are 180° apart, maximum stretching of the hoops is achieved merely be pulling the ends of the stent. Direct opposition, or opposition of exactly 180°, is not required to obtain the benefit of this construction, and it suffices that the struts not be radially aligned.

The stent wires 2 may be made of a shape memory alloy such as nitinol (or other shape memory material), pseudoelastic or superelastic alloy such as nitinol (or other pseudoelastic or superelastic material), spring metal such as stainless steel, or other suitable materials. When made of shape memory nitinol or superelastic nitinol, the stent may be trained to the shape shown in FIG. 1, and will revert to that shape either through shape memory behavior at its chosen transition temperature, or through superelastic behavior at body temperature. The appropriate compositions and training regimens may be used to obtain these characteristics. Spring materials such as stainless steel may be used also, and fabricated so that the shape of FIG. 1 is the relaxed state of the material which is regained elastically after stretching into the shape shown in FIG. 2. As with prior art stents, the stent may also be deployed by inflating a balloon within the stent.

FIG. 3 shows a cross-section of the delivery catheter for use with the hoop stent shown in FIGS. 1 and 2. The delivery catheter 13 is a multi-lumen catheter, preferably with at least two lumens, a guide wire lumen 14 and a retaining loop lumen 15. A guide wire 16 is disposed within the guide wire lumen 14 and a retaining loop 17 is disposed within the retaining loop lumen 15. The guide wire 16 may be any available guidewire, such as an 0.012 coronary guidewire, and may have an angled or curved soft tip 18 as shown. The retaining loop 17 may be any small diameter wire or thread, made of metal, suture, nylon or other suitable material. The delivery catheter 13 may be made of polyethylene, polyester or any other suitable catheter material, and may be made in convenient length (about 100–135 cm for coronary applications) and diameter (about 3 French (1 mm) for coronary applications).

The guide wire 16 is modified by the addition of a retaining hook 19 attached several centimeters proximal to the distal end of the guidewire, at a location corresponding to the distal end of both the delivery catheter 13 and the stent 1. As shown in FIG. 3, the delivery catheter has two retaining hook apertures 20d and 20p. The retaining hook exits the proximal aperture 20p and reenters the catheter through the distal aperture 20d, and the external portion 21 of the hook traps a section of the stent 1 between the retaining hook and the delivery catheter.

The retaining loop 17 is threaded through the pair of apertures 22p and 22d. The retaining loop 17 enters the retaining loop lumen through the proximal aperture 22p, and exits the lumen through the distal aperture 22d, where it loops around a portion of the wire 2 at the distal end of the stent. The proximal end 23 of the retaining loop is secured to a sliding ring 24 slidably mounted on the delivery catheter proximal end. FIG. 5 shows a radial cross-section of the delivery catheter along section 25 of FIGS. 3 and 4, with the guidewire 16 inside the guide wire lumen 14 and the retaining loop 17 within the retaining loop lumen 13.

The position of the stent 1 on the delivery catheter 13 is illustrated in FIGS. 3 and 4. The stent is stretched in order to flatten the hoops. A distal hoop 5d is retained by the retaining hook 19, while a proximal hoop 5p is retained by the retaining loop 17. Because the stent is stretched between the retaining g loop and the retaining hook, the hoops 5 and spines 7 are pulled taught against the delivery catheter, and the outer diameter of the entire assembly is reduced in comparison to the outer diameter of the expanded stent.

In use, a guiding catheter is used to catheterize the main trunk of the coronary artery (or other blood vessel to be stented). The guiding catheter is inserted percutaneously into the femoral artery and pushed into place near the coronary artery to be stented. The delivery catheter, preferably a 3 F double channel catheter with the completely stretched stent, is advanced into the lumen of the guiding catheter. The catheter-stent unit is advanced into the vessel so that the leading end of the stent can be in the right position. As a first step, the sliding ring is unlocked and moved slowly distally allowing the stent to take on its unconstrained diameter. Using the sliding ring carefully and taking advantage of the thermal memory of the stent, a smooth and controlled deployment can be achieved. At this point, some contrast can be injected via the side port of a check-flow adapter (not shown) which is attached to the guiding catheter. If the deployment is considered unsatisfactory, the retaining loop offers the chance of reposition. By pulling the sliding ring back (proximally) on the catheter, the stent can be stretched completely again. The delivery catheter's position can be changed with manipulation through the retaining loop 17, and the stent can be deployed again. When the deployment is completed, one of the strands of the retaining loop 17 is cut and the retaining loop 17 is pulled out. (Thus the retaining loop serves also as a release/retrieval loop. Note that the retaining loop 17 may be beneficially used without taking advantage of the retrieval function.) Following this maneuver, the guide wire 16 is pulled proximally within the delivery catheter to unhook the stent from the retaining hook. The guide catheter and the delivery catheter 13 are removed together completely.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device comprising:

an insertion catheter tube having a distal end, a proximal end, and at least one lumen within the tube, the insertion catheter tube having a first aperture near the distal end and a second aperture near the proximal end;

a stent, mounted upon the insertion catheter tube, comprising a plurality of hoops connected by radially opposing struts;

a first retainer, located within said at least one lumen of the insertion catheter tube and extending out the first aperture, for securing the stent to the insertion catheter tube; and a second retainer, located within said at least one lumen in the insertion catheter tube and extending out the second aperture, for securing the stent to the insertion catheter tube.

2. The device of claim 1, wherein:

the stent has an unconstrained diameter and a longitudinally stretched diameter, and the longitudinally stretched diameter is smaller than the unconstrained diameter;

the stent is mounted on the insertion catheter tube in the longitudinally stretched condition; and the stent is released from the insertion catheter tube by releasing the first retainer and the second retainer, whereby the stent expands to the unconstrained diameter.

3. The device of claim 1, wherein the stent is composed of a shape memory material.

4. The device of claim 1, wherein the stent is composed of a pseudoelastic material.

5. The device of claim 1, wherein the stent is composed of a shape memory nitinol.

6. The device of claim 1, wherein the stent is composed of a pseudoelastic nitinol.

* * * * *